(12) United States Patent
Metz-Stavenhagen

(10) Patent No.: US 7,311,733 B2
(45) Date of Patent: Dec. 25, 2007

(54) VERTEBRAL BODY PLACEHOLDER

(76) Inventor: Peter Metz-Stavenhagen, Schlossstrasse 24, Bad Wildungen (DE) 34537

( * ) Notice: Subject to any disclaimer, the term of this patent is extended or adjusted under 35 U.S.C. 154(b) by 57 days.

(21) Appl. No.: 10/515,043

(22) PCT Filed: May 19, 2003

(86) PCT No.: PCT/DE03/01607

§ 371 (c)(1),
(2), (4) Date: May 16, 2005

(87) PCT Pub. No.: WO03/096937

PCT Pub. Date: Nov. 27, 2003

(65) Prior Publication Data

US 2005/0234550 A1    Oct. 20, 2005

(30) Foreign Application Priority Data

May 21, 2002    (DE) .......................... 202 07 853 U

(51) Int. Cl.
*A61F 2/44* (2006.01)
*A61F 17/70* (2006.01)
(52) U.S. Cl. ..................................... 623/17.15; 606/61
(58) Field of Classification Search ....... 623/17–17.16; 606/61
See application file for complete search history.

(56) References Cited

U.S. PATENT DOCUMENTS 2,029,609 A * 2/1936 Burns et al. ................ 175/294
2,673,751 A * 3/1954 Finch .......................... 285/84
5,723,013 A   3/1998 Jeanson et al.
6,283,511 B1* 9/2001 Kamp ......................... 285/391

FOREIGN PATENT DOCUMENTS

| DE | 296 16 778 | 3/1998 |
| EP | 1 080 703 A | 3/2001 |
| WO | WO99 63913 A | 12/1999 |
| WO | WO 00 23013 A | 4/2000 |

* cited by examiner

Primary Examiner—David J. Isabella
(74) Attorney, Agent, or Firm—Thomas R. Vigil

(57) ABSTRACT

The invention relates to a vertebral body placeholder having a cylindrical inner body (14), which can be telescopically inserted into a coaxially arranged, sleeve-shaped outer body (16). A detent device that works in one direction is arranged between the inner body (14) and the outer body (16). A number of detent projections (22) are arranged in succession in an axial direction and form a row (20) of detent projections. A number of detent notches (26) are arranged in succession in an axial direction while corresponding to the row (20) of detent projections. Said detent notches form a row (24) of detent notches that completely or partially accommodate the row (20) of detent projections. The invention also relates to a method for assembling said vertebral body placeholder. The aim of the invention is to create a vertebral body placeholder whose overall height can be easily and reliably adjusted, particularly, during implantation. To this end, a groove (28) for accommodating the row (20) of detent projections without obstructing it is provided next to the row (24) of detent notches.

4 Claims, 3 Drawing Sheets

VERTEBRAL BODY PLACEHOLDER

DE 202 07 853.1 dated May 21, 2002

BACKGROUND OF THE INVENTION

1. Field of the Invention

The present invention relates to a vertebral body spacer having a cylindrical inner body that is telescopically slidable into a coaxially arranged, sleeve-shaped outer body.

2. Description of the Prior Art

A vertebral body spacer having a cylindrical inner body that is telescopically slidable into a coaxially arranged, sleeve-shaped outer body is known from DE 296 16 778. In order to fix said vertebral body spacer in the desired position, it can be guided through the outer body into a thread embedded in the inner body. By arranging a plurality of holes and threads in the axial direction, the vertebral body spacer can be adjusted gradually. For the operating surgeon it is however very tedious to adjust the desired size of the vertebral body spacer and to then insert said screw into the corresponding thread, particularly because the outer and the inner body are very likely to become displaced with respect to one another and because it needs a certain dexterity to insert the fixation screw into the corresponding thread.

An implant for replacing missing vertebrae is known from U.S. Pat. No. 5,723,013 in which detent lugs are formed on an inner cylinder, said detent lugs engaging into mating detent notches provided on an outer cylinder. Both the inner cylinder and the outer cylinder are each provided with two coaxially oriented slots into which a securing and fixation element may be placed as soon as the two cylinders have been brought into coincidence. The detent lugs and notches are designed in such a manner that the inner cylinder can be pulled out of the outer cylinder against the resistance of the detent lugs.

During surgical operation however it is on the one side very difficult to bring the two cylinders into coincidence in order to position the securing element and on the other side to pull the inner cylinder out of the outer cylinder against the force of the detent lug to correct the overall height of the implant.

The document EP 1 080 703 describes a telescopically extendable vertebral body spacer comprising a cylindrical inner body and a sleeve-shaped outer body that is coaxial with said inner body, said inner body being telescopically slidable into the outer body. A plurality of detent lugs arranged in four rows are provided on the outer side of said inner body, whilst at the inner side of the outer body there are provided detent notches that are also disposed in four rows, detent lugs and detent notches being designed to mate together. Between two neighboring rows of detent lugs, or rows of detent notches respectively, there is provided a free space so that the detent lugs of the inner body are adapted to be brought into the corresponding free space of the outer body while the inner body is being telescopically slid into the outer body. Once the inner body is in the desired position with respect to the outer body, the inner body (or the outer body) is pivoted to some degrees so that the detents lugs are inserted into the detent notches. In cannot be excluded that with time the inner body will pivot back and will be pushed telescopically further into the outer body as a result of the large face action thereon, which is not desired.

BRIEF SUMMARY OF THE INVENTION

In view thereof, it is the object of the present invention to provide a vertebral body spacer that reliably remains in position once said position has been found.

As a technical solution to this problem, it is proposed to provide, in a vertebral body spacer, a plurality of detent lugs forming a row of detent lugs arranged one behind the other in the axial direction with the detent lugs and mating detent notches being obliquely disposed.

A vertebral body spacer configured in accordance with this technical teaching has the advantage that later on the vertebral body spacer will not inadvertently rotate back, possibly collapsing, because the loaded vertebral body spacer presses the inner body into the deep side of the detent notches so that, for pivoting, the inner body would have to be lifted against the force acting onto the vertebral body spacer. This tends to prevent pivoting.

It has thereby been found out that it is advantageous if the detent lugs and the detent notches extend downward from the side turned toward the groove.

In another preferred embodiment, four rows of detent lugs and four rows of detent notches are equidistantly spaced on the circumference. This offers the advantage that the vertebral body spacer is evenly guided over the circumference by these four detent devices, the inner body being thus prevented from getting jammed.

In another preferred embodiment, a long hole disposed in the axial direction for continuous reception of a fixation screw As provided in the outer body. This offers the advantage that the fixation screw, which extends through the long hole, can be screwed in a corresponding thread provided on the inner body with the outer body being in any desired position with respect to the inner body.

In still another preferred embodiment, only two confronting rows of detent lugs and of detent notches are provided. As a result, the inner body can be pulled out of the outer body without pivoting. In this case, a force would be exerted through the detent lugs onto two confronting sites of the outer body so that said outer body is subjected to a brief deformation. The regions of the outer body between the rows of detent lugs thereby contract while the regions of the detent lugs are pressed radially outward until the detent lug has passed the corresponding detent notch. Next, the outer body springs back to its initial shape and the vertebral body spacer is enlarged by one detent notch. This process may be repeated several times until the vertebral body spacer has the desired size.

Further advantages of the vertebral body spacer of the invention will become apparent in the appended drawings and in the following description of embodiments thereof. Likewise, the above mentioned features and those described herein after may be used alone or in any combination with each other within the scope of the present invention. The embodiments discussed herein are merely exemplary in nature and are not intended to limit the scope of the invention in any manner.

DETAILED DESCRIPTION OF THE INVENTION

Figure 1:
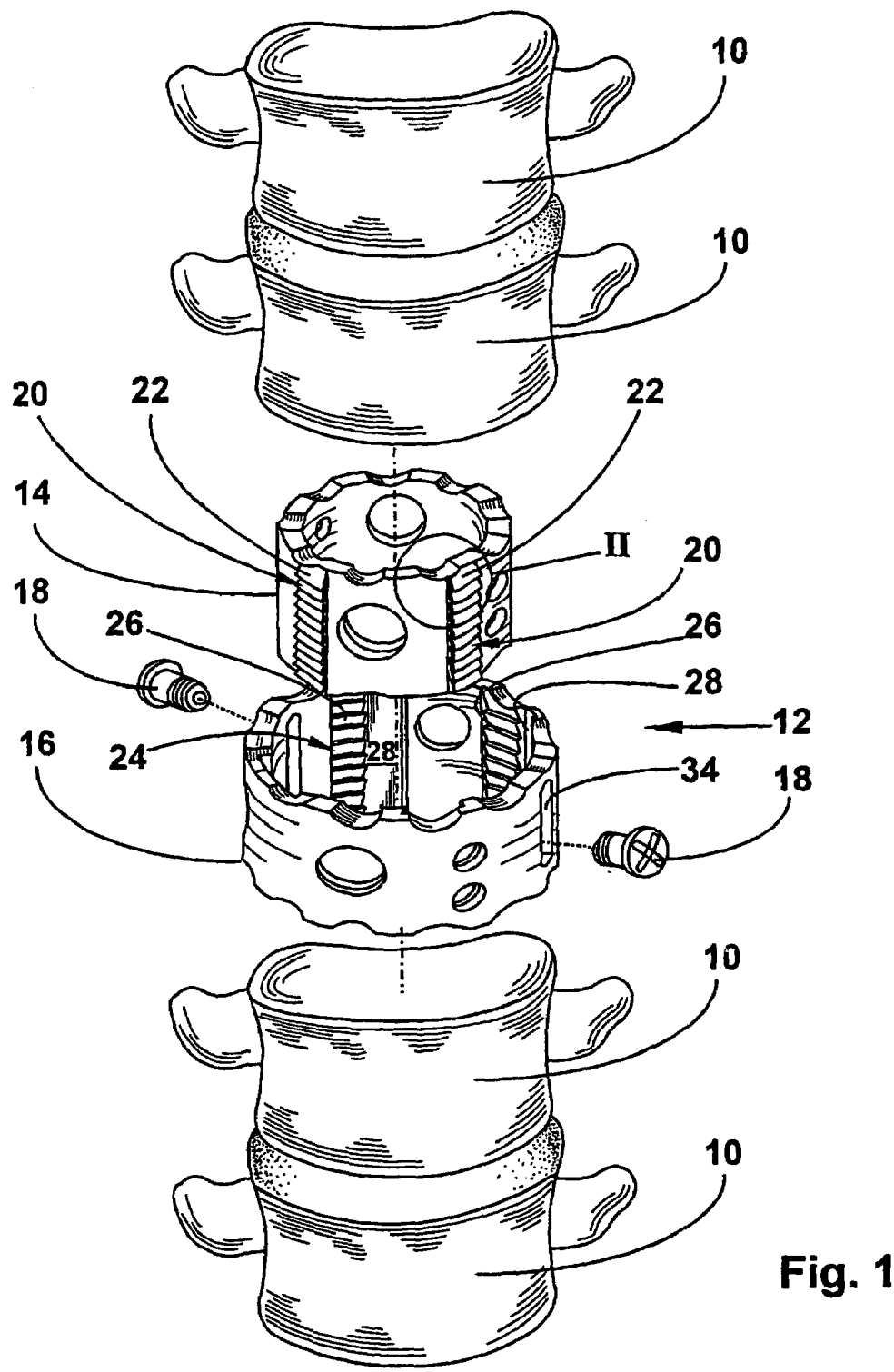
FIG. 1 is an exploded view of a spine with a vertebral body spacer according to the invention.

FIG. 1 is an exploded schematic partial view of a human spine in which there is arranged, between two vertebral bodies 10, a bipartite, cylindrical hollow spacer 12 for a vertebral body. Said spacer 12 is comprised of a smaller, cylindrical inner body 14 and of a larger, sleeve-like outer body 16 which is also cylindrical and positively and telescopically receives the inner body 14. In an effort to achieve an optimal position of the spine, the operating surgeon may fix inner body 14 and outer body 16 in the desired relative position using two fixation screws 18. A long hole 34 arranged in the outer body 16 permits to fix the spacer 12 in any position. For further details relating to spacer 12 the reader is referred to German Patent DE 296 16 778/European Patent 832 622, the full content of which is incorporated herein by way of reference.

Four rows of detent lugs 20 are provided at regular intervals around the circumference of the outer side of inner body 14, said rows being composed of several detent lugs 22 that are arranged one behind the other in axial direction. Each detent lug 22 has one substantially radially oriented stop face 32 and one slide face 30, the angle between stop face and slide face ranging between 45 and 90. degree. Four rows of detent notches 24 are spaced around the circumference on the inner side of outer body 16, each row of detent notches 24 being composed of a plurality of detent notches 26 that are arranged behind each other in axial direction. Detent notch 46 is thereby configured to match the detent lugs 22 and is also provided with a substantially radially oriented stop face and with a slide face that is arranged at an acute angle thereto. A groove 28 is formed directly beside detent notch row 24, the width and depth of which is slightly larger than the corresponding rows of detent lugs 20 so that the detent lug row 20 may be received by said groove 28 without hindrance.

Figure 2:
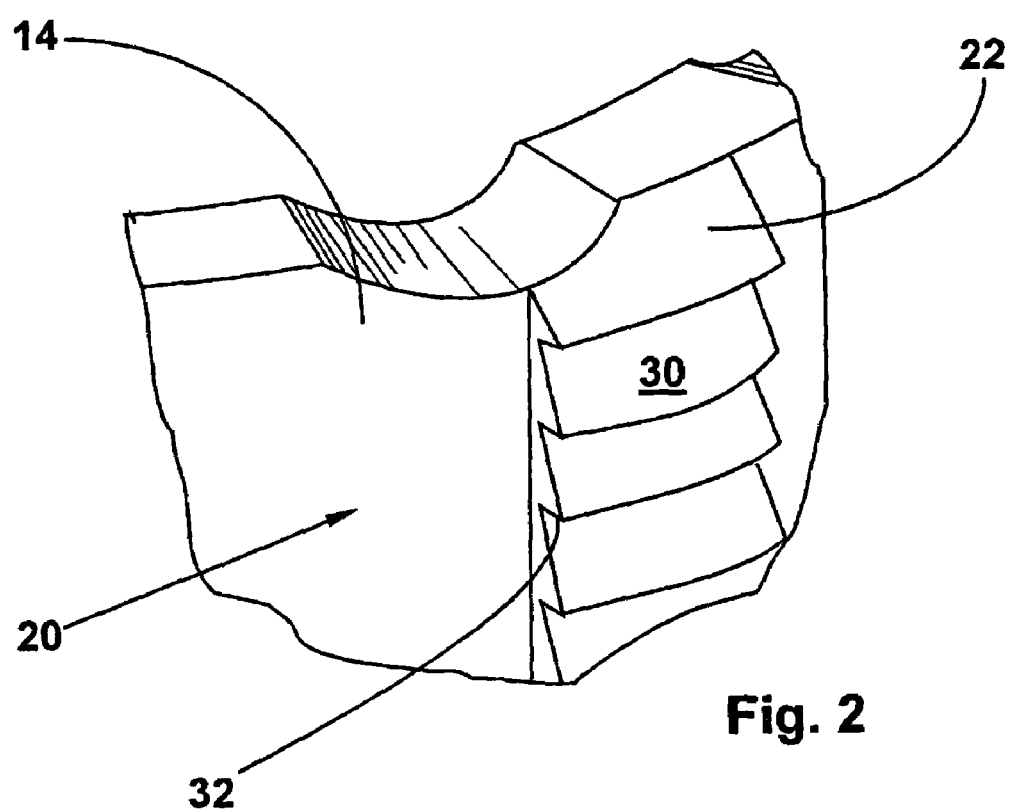
FIG. 2 is an enlarged partial view taken along the line II in FIG. 1.
Figure 3:
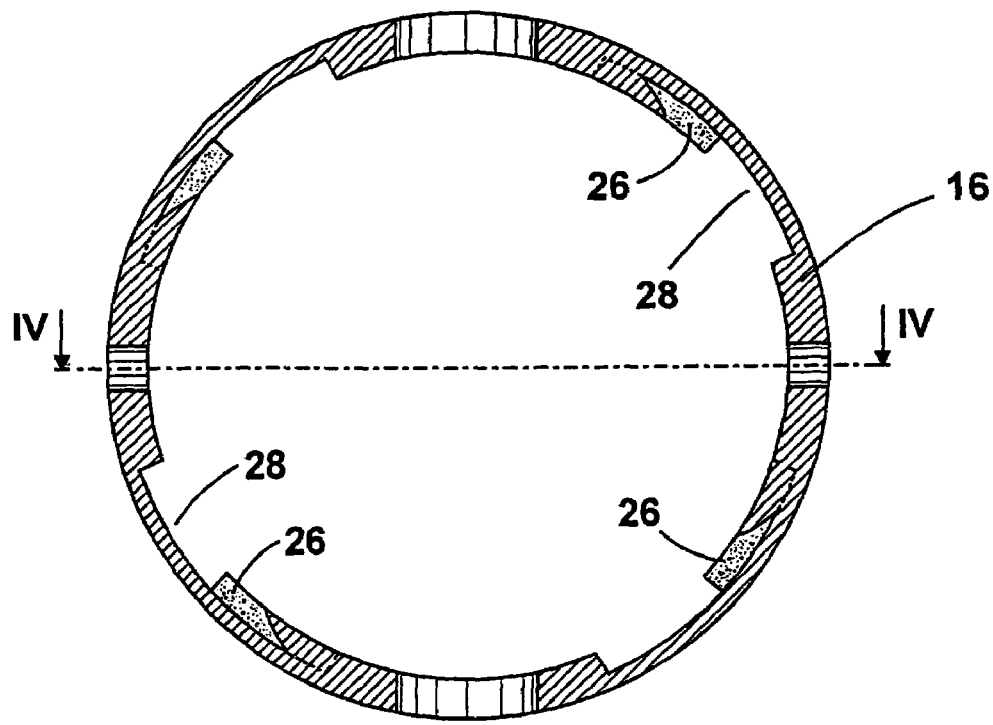
FIG. 3 is a sectional plan view of an outer body of the vertebral body spacer of FIG. 1, taken along the line III—III of FIG. 4.
Figure 4:
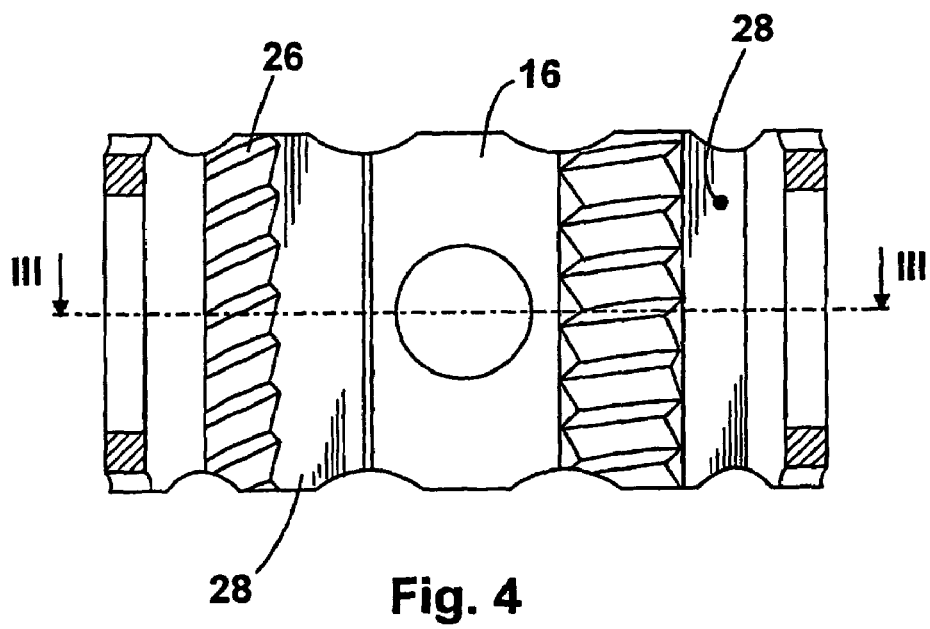
FIG. 4 is a sectional side view of the outer body of FIG. 3, taken along the line IV—IV of FIG. 3.

As illustrated in detail in the FIGS. 2 to 4, the detent lugs 22 and the detent notches 26 extend at an incline from the groove 28 downward. Taking now into consideration that the vertebral body spacer is always under load, the inner body 14 would have to be pivoted against said load to cause him to leave the position set and to return into the groove. Normally, this is not possible because of the load placed on the vertebral body spacer so that pivoting is reliably prevented.

During implantation of the vertebral body spacer in accordance with the invention, the operating surgeon proceeds as follows:

By pivoting inner body 14, the row of detent lugs 20 is removed from engagement with the row of detent notches 24 so that the row of detent lugs 20 enters the groove 28. Now, the inner body 14 may be pushed (axially) up- or downward at will in an effort to achieve preliminary coarse adjustment of spacer 12. Once the desired position has been found, the inner body 14 is pivoted back so that the row of detent lugs 20 again engages with the row of detent notches 24. The arrangement of detent lugs 22 and detent notches 26 is such that they are adjacent by their respective stop faces so that the inner body 14 is reliably prevented from slipping into the outer body 16. Once the vertebral body spacer 12 has been inserted into the desired site in the spine, the operating surgeon can repeat the procedure in order to bring the vertebral body spacer 12 into the final position desired.

In another embodiment that has not been illustrated herein, only two rows of detent lugs and of detent notches are provided. In this embodiment in particular (but also in the embodiment shown) the operating surgeon may, upon completion of coarse adjustment, pull the inner body 14 further out of the outer body 16 for the purpose of performing a fine adjustment. The slide faces of the respective detent lugs 22 and detent notches 26 thereby slide along each other until detent lug 22 snaps into the nearest notch 26. The vertebral body spacer 12 may thus be adjusted in any manner without risk of sliding back. In this position, the vertebral body spacer 12 may be secured by means of the fixation screw.

LISTING OF NUMERALS 10 vertebral body
12 vertebral body spacer
14 inner body
16 outer body
18 fixation screw
20 row of detent lugs
22 detent lug
24 row of detent notch
26 detent notch
28 groove

I claim:

1. A vertebral body spacer having a cylindrical inner body (14) that is telescopically slidable into a coaxially arranged, sleeve-shaped outer body (16), a detent device acting in one direction being disposed between the inner body (14) and the outer body (16), a plurality of detent lugs (22) forming a row (20) of detent lugs being arranged one behind the other in the axial direction, and a plurality of detent notches (26) being arranged one behind the other in the axial direction so as to correspond to the row (20) of detent lugs and forming a row (24) of detent notches for receiving in part or in whole the row (20) of detent lugs, a groove (28) for hindrance free reception of the row (20) of detent lugs being provided beside the row (24) of detent notches in the axial direction, and each lug (22) comprises one stop face (32) and one slide face 30, characterized in that the detent lugs (22) and the mating detent notches (26) are obliquely disposed and in that said stop face 32 is substantially radially oriented for easy engagement with a stop face of a notch (26) preventing premature collapse of the inner body within the outer body.

2. The vertebral body as set forth in claim 1, characterized in that the detent lugs (22) and the detent notches (26) extend at an incline from the side adjacent the row (24) of detent notches downward so as to impair potential release.

3. The vertebral body as set forth in claim 2, characterized in that two or four rows (20) of detent lugs (22) and two or four rows (24) detent notches are equidistantly space on the circumference.

4. The vertebral body as set forth in claim 1, characterized in that a long hole (34), which is disposed in the axial direction for continuous reception of a fixation screw (18), is provided in the outer body (16).

* * * * *